(12) United States Patent
Camino et al.

(10) Patent No.: US 6,368,352 B1
(45) Date of Patent: *Apr. 9, 2002

(54) LARGE TAPER MODULAR SHOULDER PROSTHESIS

(75) Inventors: Thomas S. Camino, Warsaw, IN (US); Duane G. Snyder, Scottsdale, AZ (US); David J. Urbahns, Barrington, RI (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/519,535

(22) Filed: Mar. 6, 2000

Related U.S. Application Data (63) Continuation of application No. 08/676,249, filed on Jul. 16, 1996, now Pat. No. 6,033,439, which is a continuation-in-part of application No. 08/488,585, filed on Jun. 8, 1995, now Pat. No. 5,728,161.

(51) Int. Cl.[7] .................................................. A61F 2/40
(52) U.S. Cl. .................................................. 623/19.12
(58) Field of Search ........................... 623/19.11, 19.12, 623/19.13, 22.41

(56) References Cited

U.S. PATENT DOCUMENTS

| 4,005,495 A | 2/1977 | Locke et al. |
| 4,032,994 A | 7/1977 | Frey |
| 4,624,674 A | 11/1986 | Pappas et al. |
| 4,645,506 A | 2/1987 | Link |

(List continued on next page.)

FOREIGN PATENT DOCUMENTS

| EP | 0547 369 B1 | 5/1995 |
| WO | WO 95/22302 | 8/1995 |

OTHER PUBLICATIONS

"Adaptability And Modularity In Shoulder Prostheses", Reprint from Matrise Orthopedique, Sep. 1993.
Frederick F. Buechel M.D., "Buechel–Pappas. TM. Total Shoulder System", Endotech, Inc., Jul., 1991.
Russel F. Warren, M.D. and David M. Dines M.D., "Bio–Modular. RTM. Total Shoulder", Biomet, Inc., 1992.
Charles A. Rockwood, Jr., M.D. and Frederick A. Matsen, III, M.D., "Global. T.M. Total Shoulder Arthroplasty System", DePuy Inc., 1992.
"Buechel–Pappas. TM. Total Shoulder System Implants and Instruments",Endotec, Inc., Jul., 1991.
"Equipped to Preserve", DePuy–DuPont Orthopaedics, 1993.
Frederick A. Matsen, II, M.D. and Charles A. Rockwood, Jr., M.D., "Global. TM.Total Shoulder Arthroplasty System Design Rationale and Surgical Technique", DePuy Inc., 1992.

*Primary Examiner*—David J. Isabella
(74) *Attorney, Agent, or Firm*—Maginot, Moore & Bowman, LLP (57) ABSTRACT

A kit for assembly of a modular joint prosthesis (10) includes at least two shank/body elements (22/20) sized for insertion into the shank of the bone and at least two head members (48) sized to replace one bearing surface of the joint. Each shank/body element (22/20) has a collar (58) that has a shallow width and a circular plan view and that is formed to overhang a resected level of the bone. The collar (58) has a male taper on its side wall (64). Each head member (48) has a first geometric axis (52) therethrough and defines a part spherical cavity (49) with a skirt (66) extending about the cavity (49). The skirt (66) provides a female taper for receiving and providing a mechanical connection with the male taper on the side wall (64) of each collar (58). A second axis extends (55) through the skirt (66). The first axis (52) and second axis (55) may be coincident or offset from one another.

11 Claims, 6 Drawing Sheets

U.S. PATENT DOCUMENTS

| | | |
|---|---|---|
| 4,865,605 A | 9/1989 | Dines et al. |
| 4,865,609 A | 9/1989 | Roche |
| 4,919,670 A | 4/1990 | Dale et al. |
| 4,932,974 A | 6/1990 | Pappas et al. |
| 4,995,883 A | 2/1991 | Demane et al. |
| 5,002,581 A | 3/1991 | Paxon et al. |
| 5,080,685 A | 1/1992 | Bolesky et al. |
| 5,108,437 A | 4/1992 | Kenna |
| 5,108,452 A | 4/1992 | Fallin |
| 5,135,529 A | 8/1992 | Paxon et al. |
| 5,181,928 A | 1/1993 | Bolesky et al. |
| 5,314,479 A | 5/1994 | Rockwood, Jr. et al. |
| 5,358,526 A | 10/1994 | Tornier |
| 5,370,706 A | 12/1994 | Bolesky et al. |
| 5,413,603 A | 5/1995 | Noiles et al. |
| 5,489,309 A | 2/1996 | Lacket et al. |
| 5,507,817 A | 4/1996 | Craig et al. |
| 5,507,830 A | 4/1996 | DeMane et al. |
| 5,728,161 A * | 3/1998 | Camino et al. ......... 623/22.41 |
| 6,033,439 A * | 3/2000 | Camino et al. ......... 623/16.11 |
| 6,120,542 A * | 9/2000 | Camino et al. ......... 623/18.11 |

* cited by examiner

LARGE TAPER MODULAR SHOULDER PROSTHESIS

CROSS-REFERENCE TO RELATED APPLICATIONS

This application is a continuation of U.S. application Ser. No. 08/676,249, filed Jul. 16, 1996, now U.S. Pat. No. 6,033,439, which is in turn a continuation-in-part of U.S application Ser. No. 08/488,585, filed Jun. 8, 1995, now U.S. Pat. No. 5,728,161. Note that U.S. application Ser. No. 08/676,249 is a U.S. national phase counterpart of international application Ser. No. PCT/US96/10045 filed Jun. 7, 1996, which claims priority to U.S application Ser. No. 08/488,585, filed Jun. 8, 1995. The disclosures of each of the foregoing patent applications are hereby incorporated by reference for all purposes.

BACKGROUND AND SUMMARY OF THE INVENTION

This invention relates to improvements in joint prostheses. It is disclosed in the context of a shoulder prosthesis but is believed to have utility in other applications as well.

There are several prostheses that employ, as part of their systems for joining prosthesis components, tapered locking joints such as Morse tapered joints and the like. There are also the systems illustrated and described in U.S. Pat. Nos.: 5,080,685; 5,181,928; 5,314,479; 4,932,974; and 4,624,674; European Patent Specification 0,547,369 B1; Buechel-Pappas™ Total Shoulder System Implants and Instruments; and, Buechel-Pappas™ Total Shoulder System Surgical Procedure by Frederick F. Buechel M.D. No representation is intended that a thorough search of all material prior art has been conducted or that no more material prior art exists. Nor should any such representation be inferred. The disclosures of the '685, '928 and '479 patents are incorporated herein by reference.

A significant concern in the design of joint prostheses is weight. Particularly the bearing surfaces of such prostheses must be made of durable materials, with such alloys as cobalt chrome being preferred by many physicians. Titanium, while it is lighter, is not as durable as cobalt chrome. So, titanium is not an acceptable substitute for many prosthetic joint bearing surfaces. The generally competing desires for light weight and durability have led to several multiple component prostheses. In such prostheses, components that do not provide bearing surfaces are fabricated from somewhat less durable but typically more lightweight materials such as, for example, titanium. Components that provide bearing surfaces are fabricated from somewhat more durable but typically heavier weight materials such as, for example, cobalt chrome. A problem with many such prostheses is that they are designed without optimal regard for the durability-weight tradeoffs. Consequently, many bearing components are designed for greater strength than is necessary under the circumstances. An example would be a shoulder prosthesis, the head member of which is constructed from cobalt chrome and the body/shank element of which is made from titanium alloy. Although the head is constructed from extremely durable cobalt chrome, it is a thick-walled component, making it heavier than necessary to perform its bearing function. The head's thick-walled design is related in part to the manner in which it is joined to the body/shank element of the shoulder prosthesis. Usually this involves multiple butt joint and/or tapered surfaces and threaded fasteners, all of which add to the weight of the prosthesis.

Another significant consideration in the design of such joint prostheses is range of motion. Designs strive to achieve the natural range of motion of a healthy joint. How the head member and body/shank element are joined in the shoulder prosthesis example described above, clearly affects the range of motion available in said prosthesis. In a few of the shoulder joint prostheses identified above, for example, some potential bearing surface on the humeral component's head is lost. Such loss is due to the technique used to connect the head to the body/shank element of said humeral component.

Yet another significant consideration in the design of such joint prostheses is the positioning of the head on the body/shank portion to achieve a natural shoulder joint alignment. This alignment varies from patient to patient. Therefore, some designs have securing pins that fix an eccentric alignment of the head upon a spacer. See for example U.S. Pat. No. 5,358,526. These pins can add to the weight of the head. What is needed is a modular shoulder prosthesis that has a lighter weight head member whose alignment on the shank element can be adjusted easily by the caregiver to provide a custom-fit orientation for each patient and that itself cooperates with the body/shank to lock into a secure and fixed position.

It is an object of the invention to provide a lighter weight configuration for a prosthesis.

It is another object of the present invention to provide a design for a multiple component joint prosthesis that makes more effective use of potentially available joint bearing surface.

It is another object of the invention to provide a multiple component joint prosthesis that has a head member formed for eccentric alignment on a shank/body element.

Yet another object of the invention is to provide a multiple joint prosthesis that has a collar that prevents sliding movement of the prosthesis into the medullary passageway of a bone and taper-locks a head member in a fixed position thereon.

It is still another object of the present invention to provide a joint prosthesis having a head member formed for eccentric alignment on a shank/body element and for taper-locking engagement on the shank/body element.

According to an aspect of the invention a kit for assembly of a modular joint prosthesis that can replace a head, neck, and adjacent portions of a bone of the joint comprises at least two shank/body elements. Each element is sized for insertion into the shank of the bone. At least two head members are also provided. Each head member is sized to replace one bearing surface of the joint. In addition, each shank/body element comprises an upper collar that lies superimposed on the resected level of the bone in the completed prosthetic joint. The collar provides a male taper at its outer diameter. Each head member has a first geometric axis therethrough. Moreover, the head member defines a part spherical cavity and includes a skirt extending about the cavity. The skirt provides a complementary female taper for receiving the male taper of each shank/body element. A second geometric axis extends through the skirt along its central geometric axis. The first and second axis may be coincident in accordance with the present invention. The second axis is, however, offset from the first axis in preferred embodiments to enable the head member to undergo eccentric alignment on the collar. Engagement of the female taper on the male taper provides a mechanical connection between the head and the shank/body element that may be the sole mechanical connection in the preferred embodiments. It will be appreciated, however, that one skilled in the art may find additional techniques for supplementing the taper lock connection without departing from the scope of this invention.

According to another aspect of the invention, a joint prosthesis consists essentially of an integral shank and body. The body includes a collar having a male taper toward a complementary bearing surface to the prosthesis. A head has a geometric axis therethrough and a female taper defining a second geometric axis that may be coincident with the first axis or offset from the first axis in preferred embodiments. The female taper is complementary to the male taper of the collar to receive the collar in the assembled joint.

According to another aspect of the invention, a joint prosthesis comprises a first component and a second component. This second component consists essentially of an integral shank and body. The body includes a collar having a male taper toward the first component in the assembled joint. The second component consists essentially of a head having a geometric axis therethrough and a female taper complementary to the male taper of the collar. The female taper may be in concentric alignment with the head member about the geometric axis. However, the female taper is offset from the geometric axis in preferred embodiments. This female taper is formed to receive the collar in the assembled joint.

According to another aspect of the invention, a joint prosthesis assembly that can replace a head, neck, and adjacent portion of a first bone of the joint removed at a resected level comprises a head member and a shank/body element. That element comprises a body element with a shank element extending downwardly therefrom. The shank element is formed to be received in a shank of the resected first bone. The body element includes a collar portion to be adjacent the resected level. The collar portion has a radially outer peripheral surface. This outer surface provides a peripheral engaging surface extending away from the resected level toward an opposite bearing surface of a second bone of the joint. A head member provides a spherical outer bearing surface facing the opposite bearing surface and having a geometric axis extending therethrough. The head member also includes an inner surface having, at its radially outer extent, a corresponding peripheral surface. This peripheral surface engages the collar engaging surface after the shank/body element is installed in the shank of the bone. The peripheral engaging surface also defines a second geometric axis therethrough. The second axis may be coincident with the first axis or, in preferred embodiments, offset and substantially parallel to the first axis. The engaging surfaces provide a mechanical connection between the head member and the shank/body element that may be the sole connectors.

Additional objects, features and advantages of the invention will become apparent to those skilled in the art upon consideration of the following detailed description and preferred embodiments exemplifying the best mode of carrying out the invention as presently perceived.

BRIEF DESCRIPTION OF THE DRAWINGS

FIG. 12 illustrates a fragmentary sectional view, taken generally along section lines 12—12 of FIG. 10;

FIG. 12a illustrates an alternative detail to the detail illustrated in FIG. 12;

FIG. 13 illustrates a fragmentary longitudinal sectional view of an alternative detail to the details illustrated in FIGS. 11, 12 and 12a;

FIG. 14 illustrates a fragmentary sectional view taken generally along section lines 14—14 of FIG. 13;

DETAILED DESCRIPTION OF THE DRAWINGS

Figures 1, 2, 3, 4:
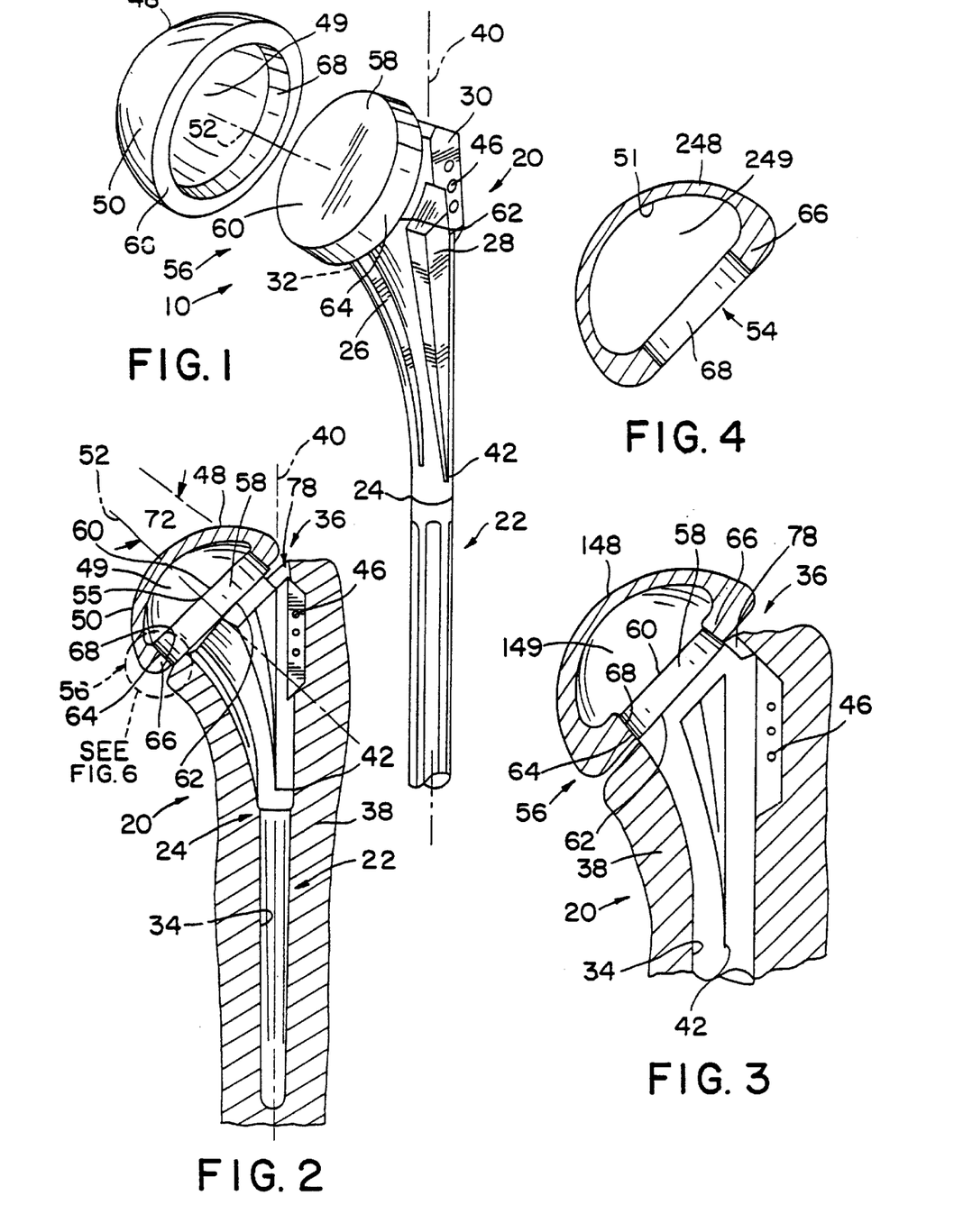
FIG. 1 illustrates a fragmentary exploded perspective view of an apparatus constructed according to the invention.
FIG. 2 illustrates a fragmentary longitudinal sectional view through the apparatus of FIG. 1 assembled.
FIG. 3 illustrates a fragmentary longitudinal sectional view through an apparatus according to the present invention.
FIG. 4 illustrates a longitudinal sectional view of an alternative detail to a detail of the apparatus illustrated in FIGS. 1–3.

Referring now to FIG. 1, a shoulder prosthesis 10 includes a humeral body element 20, a shank element 22, and a head member 48. This head member 48 is formed to be mounted on the body element 20. The body element 20 can be formed integrally with, or as a separate component from the shank element 22. If the two elements 20, 22 are formed separately, any suitable means such as welding, soldering, threaded engagement, either with or without (a) suitable adhesive(s), or the like can be used to join them together at a joint 24. See FIG. 1.

Figures 8, 9, 10, 11:
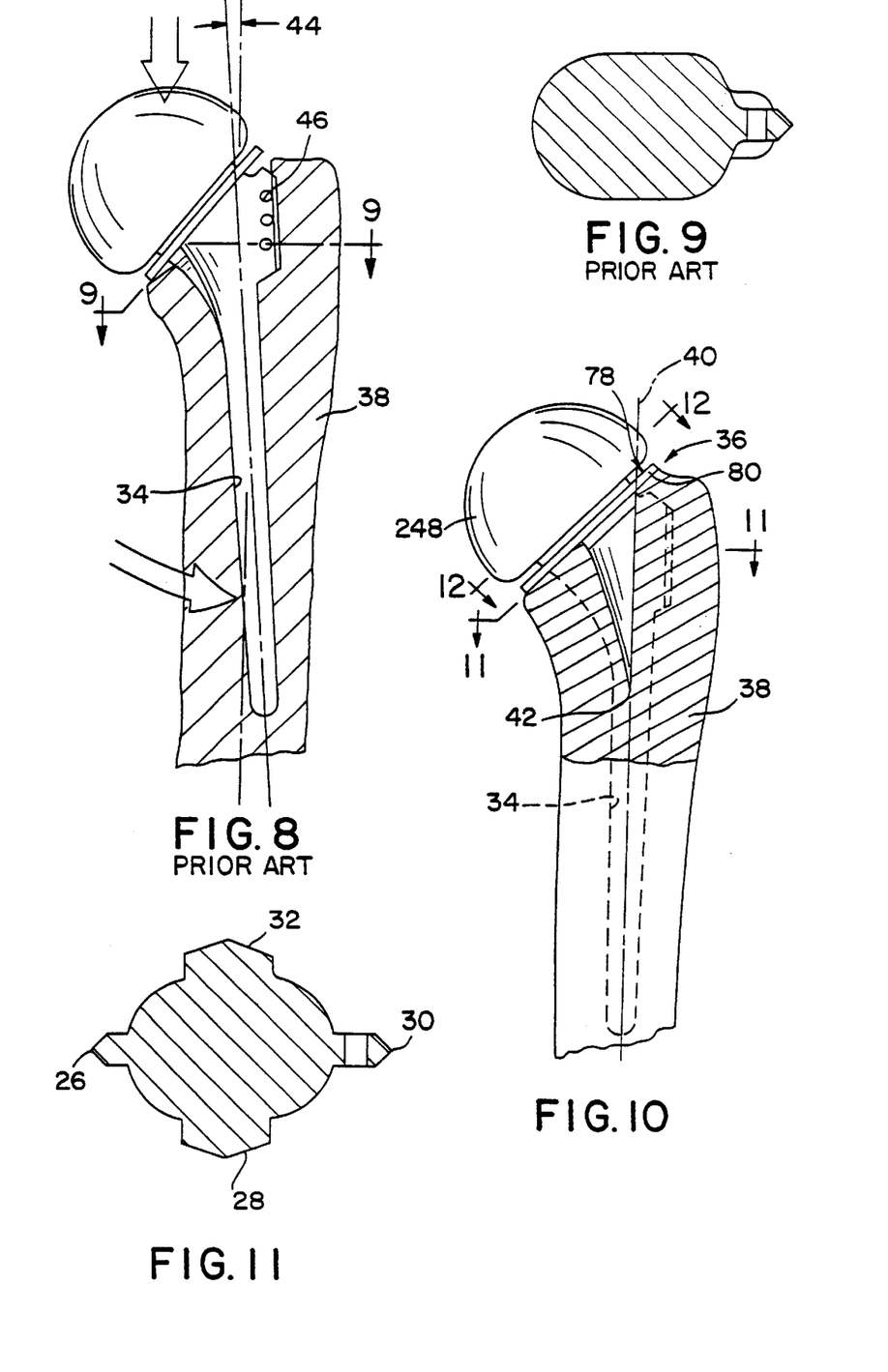
FIG. 8 illustrates a fragmentary longitudinal sectional view through a prior art device illustrating a problem addressed by the present invention.
FIG. 9 illustrates a fragmentary sectional view, taken generally along section lines 9—9 of FIG. 8.
FIG. 10 illustrates a fragmentary longitudinal sectional view of an apparatus constructed according to the invention.
FIG. 11 illustrates a fragmentary section view, taken generally along section lines 11—11 of FIG. 10.

The body element 20 is provided with ribs 26, 28, 30 and 32. Ribs 26, 28, 30 and 32 guide the humeral body 20 and shank 22 as they are inserted into a medullary passageway 34 from the prepared proximal end 36 of the humerus 38. Ribs 26 and 30 are generally straight sided ribs that extend generally parallel to the centerline 40 of shank 22. Ribs 28 and 32 on the other hand are somewhat wedge-shaped. Each rib 28, 32 is slightly larger or thicker adjacent the proximal end 36 of humerus 38 and tapers generally to a point 42 that is positioned distally therefrom. See FIG. 2. Such configuration aids the shank 22 in reducing the tendency, illustrated in FIGS. 8–9, of prior art humeral components to become tilted 44 in a varus-valgus direction during insertion into the medullary passageway 34 in the humerus 38. One or more of ribs 26, 28, 30, 32 can be provided with suture openings 46 in accordance with current practice. These openings 46 are useful in the repair of certain kinds of soft tissue injuries and disease. The shank/body element 22, 20 may be constructed from relatively light weight, relatively less durable material such as titanium.

The humeral component is also provided with the part spherically shaped head member 48. The required portion 50 of a spherical surface defined by head 48 varies from person to person and for this reason, kits containing a number of head portions 48, 148, 248, 348, 448, 548, 648, and so on having shallower and deeper cavities 49, 149, 249, 349, 549 and so on can be provided in kits. See FIGS. 1, 3, 4, 7, 12a, and 13. For this same reason, such kits can contain more than one stem/body portion 22, 20; 122, 120; 222, 220 and so on. Alternatively, if a detachable stem body portion 22, 20, 122, 120, 222, 220 configuration is employed, different numbers (for example, only one) of body(ies) 20, 120 and stems 22, 122, 222 can be provided. See FIGS. 1, 3, 13 and 14. While only one head member 48, body 20, and stem 22 will be discussed hereafter, except with reference to preferred embodiments, it will be appreciated that a plurality of head members 48, 148, 248, 348 . . . , bodies 20, 120, 220 . . . , and stems 22, 122, 222, 322 . . . may be provided in a kit for assembly of a shoulder prosthesis. The head portions 48 illustratively are constructed from durable material such as, for example, a cobalt chromium alloy. Although such materials typically are somewhat heavy, weight is optimized by the thin wall construction of heads 48 with their attendant generally part spherical cavities 49.

Figures 5, 6, 7:
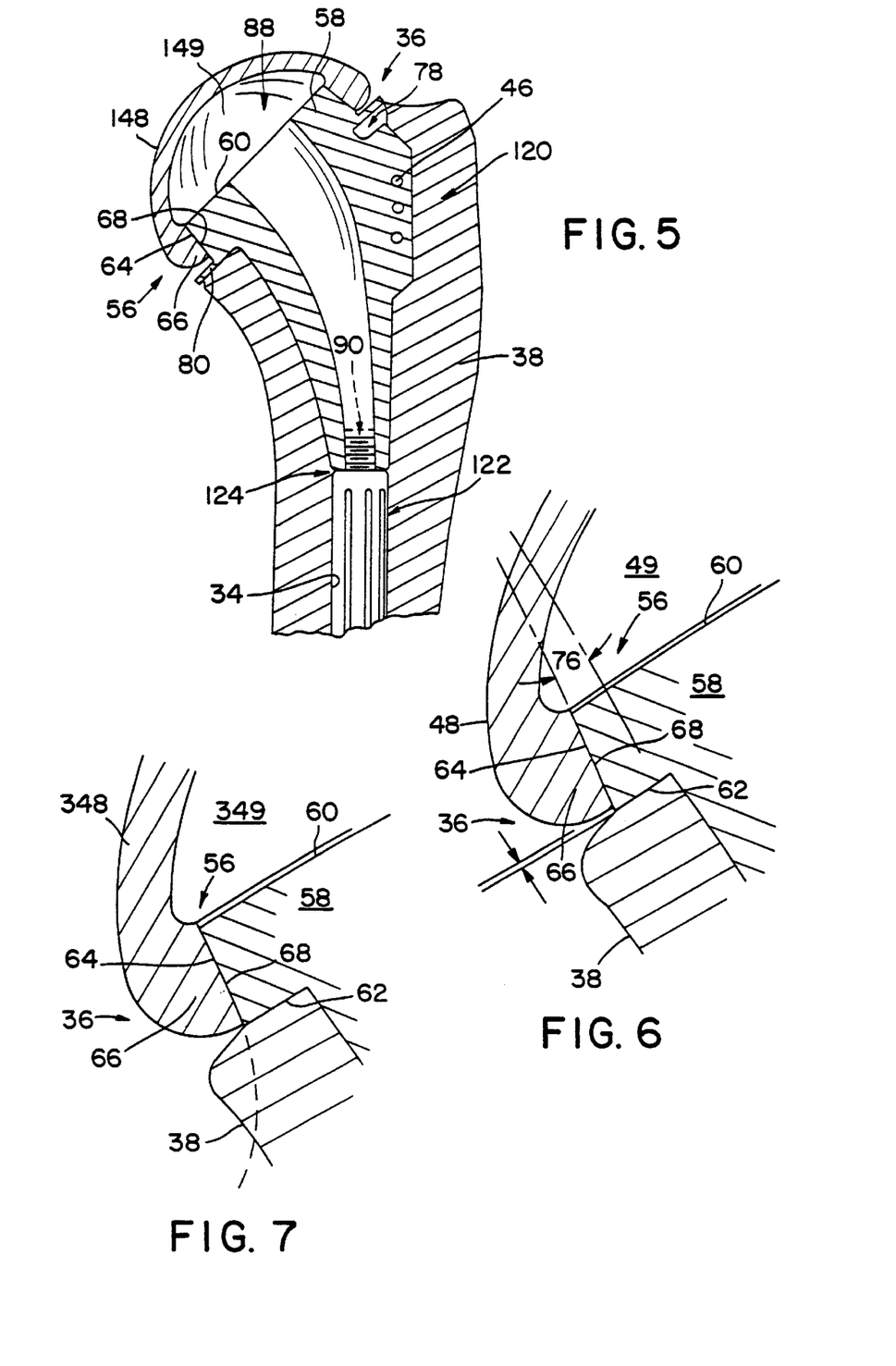
FIG. 5 illustrates a fragmentary longitudinal sectional view through an apparatus according to the present invention.
FIG. 6 illustrates a much enlarged fragmentary longitudinal sectional view through an apparatus according to the invention.
FIG. 7 illustrates a fragmentary longitudinal section view of an alternative detail to the detail illustrated in FIG. 6.

In any event, an attachment mechanism 56 is provided to couple any head member 48 to the body 20 of any shank/body element 22/20. See FIG. 1. Attachment mechanism 56 includes a disk-shaped collar 58 of uniform size and shape formed at the proximal end of each shank/body element 22/20. The collars 58 are shallow in width and circular in plan view. Collars 58 have a smaller circle or upper disk portion 60 more proximal to the glenoid in an assembled prosthetic joint and a larger circle or lower disk portion 60 more remote from the glenoid in an assembled prosthetic joint. A radially outer perpherial surface or sidewall 64 of each collar 58 extends between the larger circle 62 and the smaller circle 60. Preferably, the side wall 64 converges from the larger circle 62 toward the smaller circle 60 to provide an exterior or male taper. The taper may also be a curve, for example, exponential, a curve of a conic section—circle, ellipse, parabola, hyperbola or the like, as illustrated in FIG. 7. This disk-shaped collar 58 is formed to minimize its thickness or height while maximizing its diameter or width. For example, a preferred collar has a thickness height of about 0.1 to about 0.025 inches (0.25 cm–0.64 cm) and a diameter, of the large circle 62 of about 0.8 inches (2.0 cm). Thus, the disk-like collar 58 has an axial depth of about ⅛ to about ¼ of the diameter of the largest diameter of the collar 58. It is understood that the overall diameter of the collar 58 may vary in order to be received by variety of head members 48. Importantly, the large circle 62 of the collar 58 is sized to overhang, or be superimposed on the resected level 78 of the bone. See FIGS. 2, 6, 7, 19 and 20. The superimposed positioning of the collar 58 on the bone substantially prevents the shank/body element 22, 20 from sinking into the medullary passageway 34 in the humerus 38.

Figure 20:
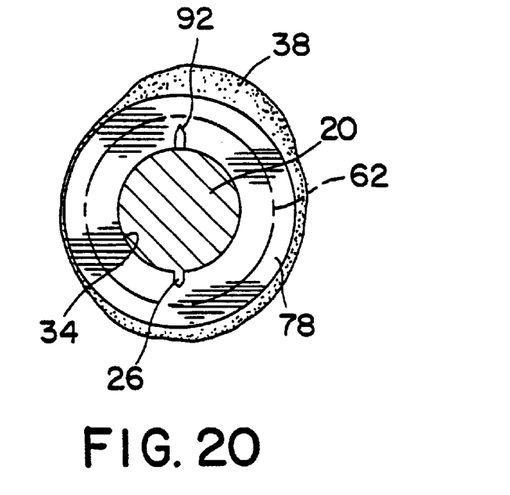
FIG. 20 illustrates a view taken along lines 20—20 of FIG. 19.

Referring now to FIG. 20, the large circle 62 of the collar 58 presses against the resected level 78 of the bone. Generally, the large circle 62 extends 360° about the medullary passageway 34 that receives the shank/body element 22/20. This engagement substantially stabilizes the shank/body element 22/20 in the bone. Grooves or cuts 92 are made in the humerus 38 bone during insertion of the shank 22 in the medullary passageway 34 and that the resected level 78 is not always a smooth planar surface. Therefore, it is understood that the large circle 62 of the collar 58 will not necessarily press against the resected level 78 at all points a full 360° about the axis 55. However, the engagement of the collar 58 and humerus 38 at the resected level 78 will serve to block both sliding movement and tilting of the prosthesis 10 in the bone.

The head members 48 of any kit have a geometric axis 52 therethrough and are selectively mounted on one of the collars 58. The heads 48 may be constructed from a durable material such as, for example, a cobalt chromium alloy. Although such materials typically are somewhat heavy, weight is optimized by the thin wall construction of heads 48, with their attendant generally part spherical cavities 49. Each of the head members 48 of any kit are further provided with a concave inner surface 51 having, at its radially outer extent, a peripheral surface or skirt 66. The skirts 66 have side walls 68 defining an opening 54 therethrough that is sized to receive at least a portion of the side wall 64 of the collar 58 therein. The opening 54 leads to the part spherical cavity 49. See FIGS. 1, 4, 15 and 16. The second geometric axis 55 extends through the center of the opening 54 and thus through the skirt 66. As shown in FIGS. 1–14 this second axis 55 may be coincident with the first geometric axis 52. In an alternative embodiment the second axis 55 is spaced-apart from the first geometric axis 52. See FIGS. 15–19. This offset positioning of the second axis 55 from the first axis 52 results in eccentric alignment of the head member 48 on the shank 20.

Figures 15, 17:
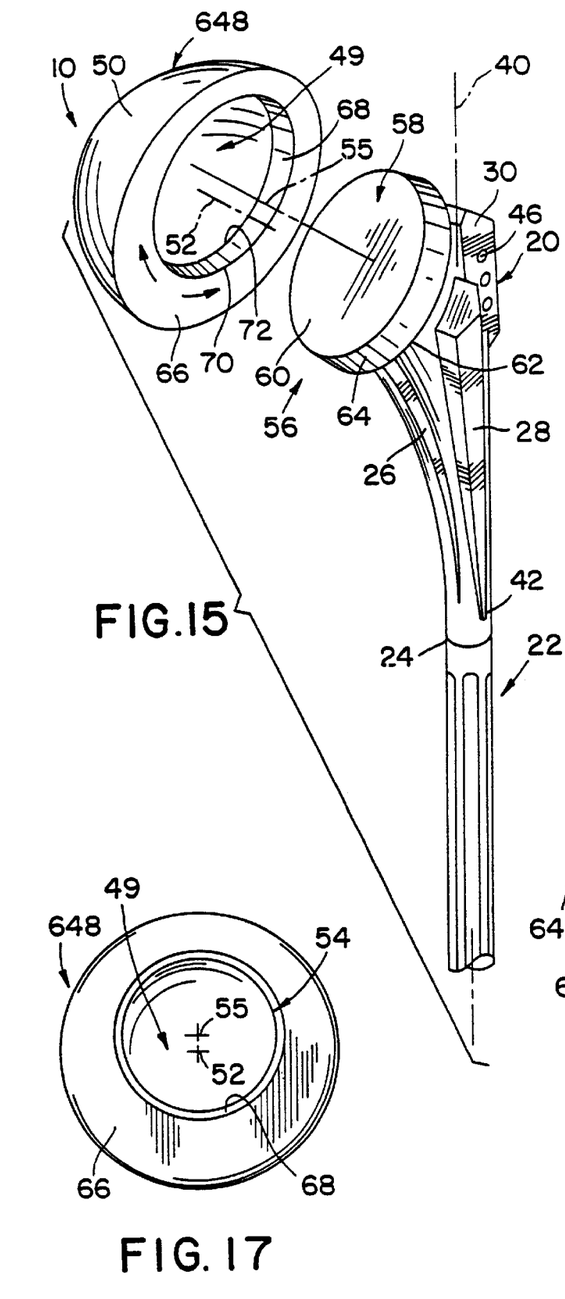
FIG. 15 illustrates a fragmentary exploded perspective view of an alternative apparatus constructed according to the invention.
FIG. 17 illustrates a view taken along lines 17—17 of FIG. 16.
Figure 16:
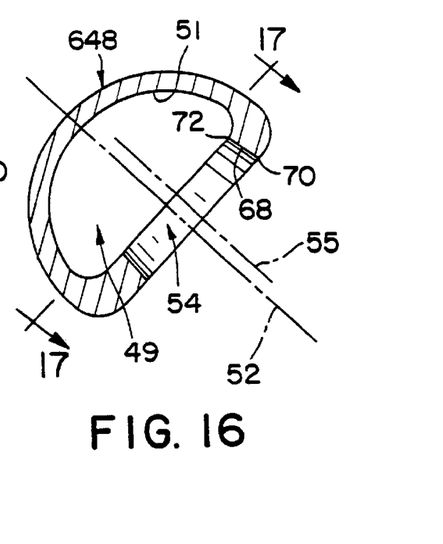
FIG. 16 illustrates a longitudinal sectional view of a detail of the apparatus illustrated in FIG. 15.
Figure 19:
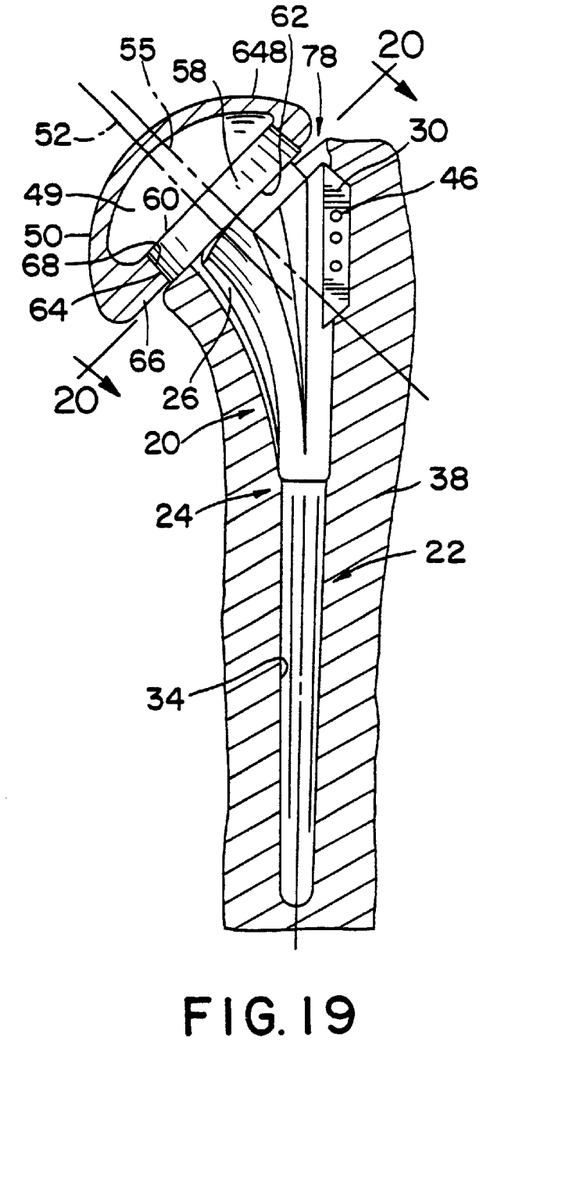
FIG. 19 illustrates a fragmentary longitudinal sectional view through the apparatus of FIG. 15, assembled.

The interaction between the collar 58 and the skirt 66 blocks rotation of head member 48 about axis 52 after the caregiver has selected a custom-fit orientation. Such interaction also serves to securely lock the head member 48 on the attachment mechanism 56 of the collar 58. As shown in FIGS. 15 and 19 the skirt 66 has an outer ring 70 and an inner ring 72. The walls 68 provide complementary interior or female tapers that are sized to engage and lock with the male taper on side wall 64. If the tapers of walls 64 in any kit are straight, the tapers of the walls 68 of the head members 48 in that kit are also straight. If one set 64 of tapers are parabolic sections, the other set 68 of tapers are complementary parabolic sections, and so on.

The length of the male taper on side wall 64 and axial depth of the female taper may vary and do not materially affect the locking capabilities of the collar 58 and sidewall 64. Importantly, the axial depth of the female taper is typically less than the length of the side wall 64. Therefore, when assembled, the side wall 64 extends slightly below the level of the skirt 66. See FIG. 19. This positioning substantially prevents engagement of the skirt 66 with the humerus 38. Typically the head member 48 is situated about 0.01 to about 0.04 inches (0.02 to about 0.1 cm) above the large circle 62.

The tapers 64, 68 are locking tapers. That is, in straight, symmetric tapers, the included angle between diametrically opposite points on the collar 58 will be greater than zero degrees and less than or equal to fourteen degrees. In symmetrically tapered wall 68, the angle between the outer rim 70 and the inner rim 72 is greater than zero degrees and less than or equal to seven degrees. A curved taper can be achieved if the acute angles between tangents to the curve over much of its length and perpendicular to the surfaces 60, 62 are greater than zero degrees and do not exceed seven degrees. Therefore, in the preferred embodiment the interaction between side walls 68 and 64 provide the sole mechanical connection between head member 48 and body 20. Such a taper-lock attachment prevents both detachment of the head member 48 from the body 20 and rotation of the skirt 66 about the second geometric axis 55.

In preferred embodiments, the head member 48 is formed for eccentric alignment on the body element 20. The second axis 55 is offset from the first geometric axis 52 to allow for selective eccentric alignment of the head member 648 on the body element 20 at any one of an infinite number of selectively variable angular positions about the second axis 55. While only one head member 648 is illustrated, it will be appreciated that a plurality of head members 48 of different shapes and sizes may be provided in a kit for assembly with a body element 20.

The head member 648 may be positioned 360° about the second axis 55 on the collar 58. See FIG. 18. Thus, as positioning occurs, the first geometric axis 52 revolves about said second axis 55. See, for example the relative positioning of axis 55 as shown by a pre-determined radius 57 in FIG. 18. Revolving the second axis 55 about the first geometric axis 52 of the head member 648 allows the caregiver to custom-select the angular position of the head member (as shown, for example in phantom). Thus, the head member 48 can be mounted on the collar 58 in any number of positions about the second axis 55.

In the preparation of the proximal end 36 of humerus 38 to receive a prosthesis according to the invention, the proximal end 36 is resected. The caregiver inserts the assembled shank 22 and body 20 into the resected humerus 38 until it is stopped by the engagement of the surface 62 of collar 58 with the humerus 38. See, for example, FIG. 20. Thus, the surface 62 (in phantom) overhangs the resected surface 78 and engages the humerus 38. The head member 48 is then aligned with the collar 58 of the body 20 such that the female and male tapers are not engaged. Head member 48 is then taper locked into a secure locked engagement on the collar 58. Generally, the collar 58 will be thick enough to allow full engagement of the side wall 68 with some of the wall 64 of the collar 58. This engagement will prevent interference of proximal end 36 of humerus 38 with skirt 66 and insure maximum retention of head member 48 on collar 58. This can further be insured by provision of an illustratively circular flange 80 adjacent collar 58. Se FIG. 5.

Figure 18:
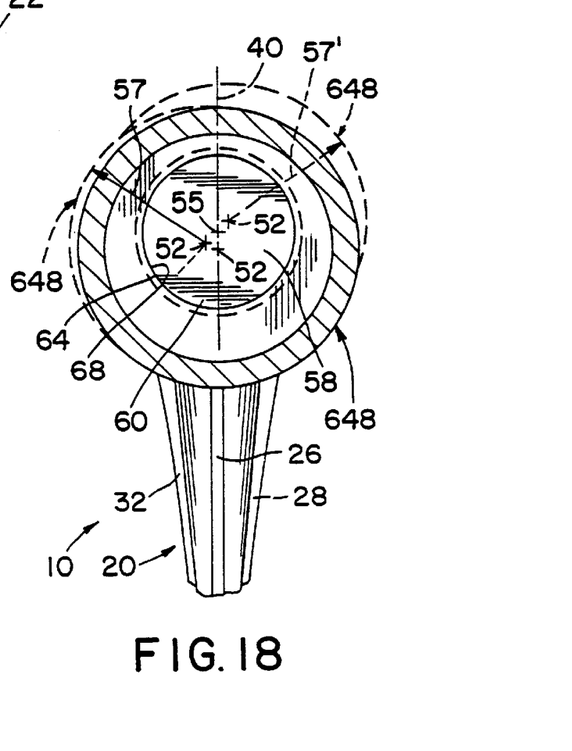
FIG. 18 illustrates a longitudinal view with portions broken away of the apparatus of FIG. 15, assembled.

In preferred embodiments, prior to locking the head member 48 on the collar 58 the caregiver can situate the head member 648 in an offset position as shown in phantom in FIG. 18. This alters the positioning of the geometric axis 52 of the head member on the collar 58. Moreover, such positioning can continue until the head member 648 is positioned in a suitable eccentric alignment for the particular patient.

Therefore, the kit of the present invention provides a modular shoulder prosthesis having at least one but preferably at least two or more shank/body element 22,20 and at least one, but preferably at least two or more light-weight durable head members 48. In preferred embodiments, the head member 48 is aligned on the element 22, 20 in a variety of eccentric positions. Moreover, the head member 48 itself cooperates with the shank/body element 22, 20 to taper-lock said member 48 and element 22, 20 together. The taper-lock provides a mechanical connection therebetween.

Referring now to FIGS. 5, 12, 12a, 13 and 14, venting of the cavity 49 during installation of head portion 48 onto collar 58 is achieved by providing one or more of a discontinuity 84 in wall 68 (FIG. 12), a discontinuity 86 in wall 64 (FIG. 12a), and a passageway 88, 188 through collar 58 from surface 60 to a remote location 90, 190 on stem/body portion 22/20.

Figures 12, 12A, 13, 14:
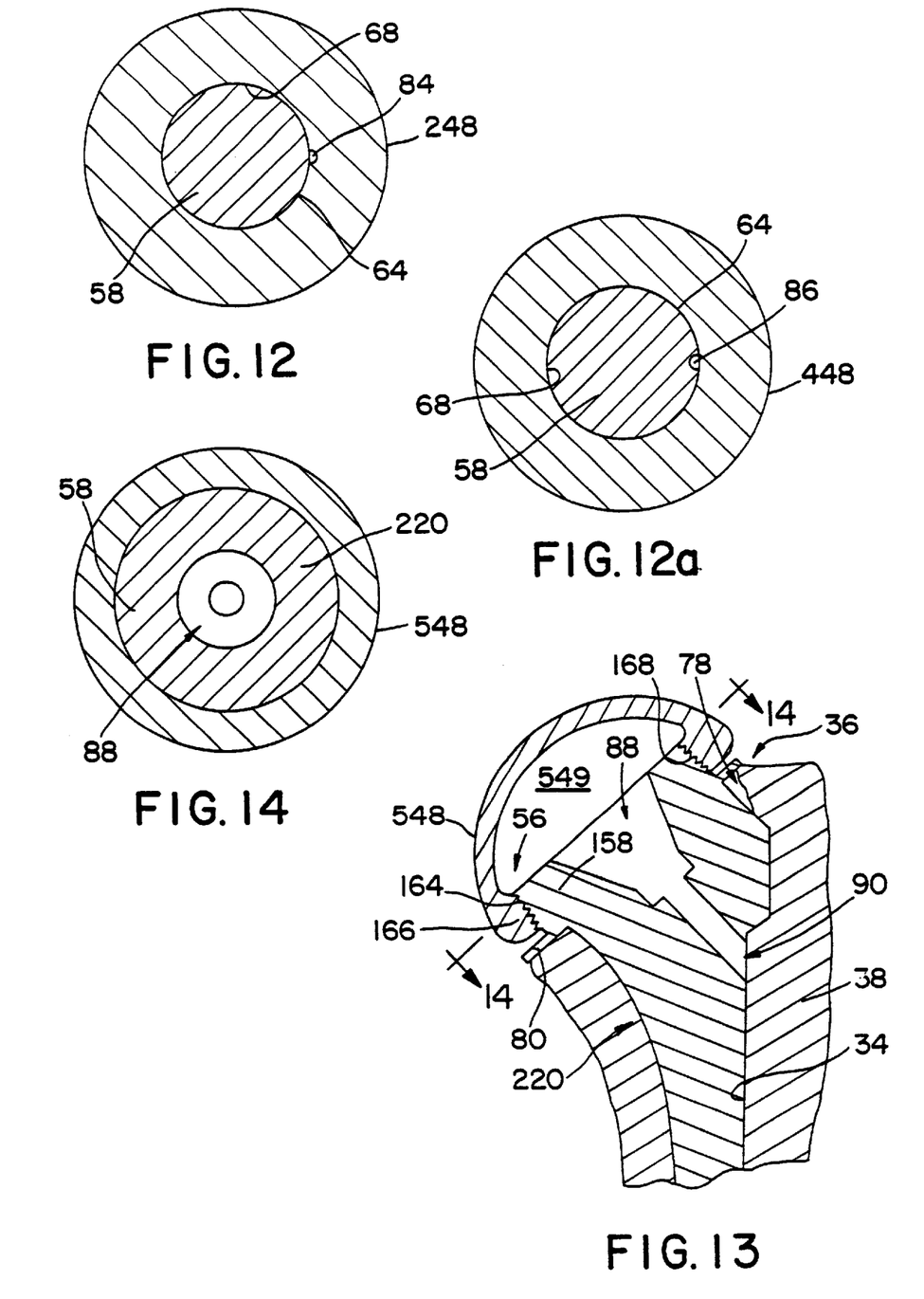

Alternative forms of standard attachment mechanism 56 are also contemplated. For example, and as illustrated in FIG. 13, complementary threads 164, 168 are provided on the outer wall of collar 158 and the inner wall of skirt 166, respectively.

Although the invention has been described in detail with reference to certain preferred embodiments, variations and modifications exist within the scope and spirit of the invention as described and defined in the following claims.

What is claimed is:

1. A kit for assembly of a modular joint prosthesis for replacement of a head, neck and adjacent portions of a bone of the joint, the kit comprising:
   at least two shank/body elements, with each element sized for insertion into the shank of the bone, each shank/body element comprising an upper collar to lie adjacent the resected level of the bone, said collar having a first circular portion formed to overhang the resected level of the bone, a second circular portion spaced apart from the first circular portion, and a side wall at an outer diameter of the collar, the side wall extending between the first portion and the second portion and providing threads thereon; and
   at least two head members with each head member sized to replace one of the bearing surfaces of the joint, each head member defining a cavity having a geometric axis therethrough and providing a skirt defining an opening having a second axis therethrough that is offset relative to the geometric axis, the skirt further providing corresponding threads for receiving the threads of the collar of each shank/body element, the engagement of the threads providing a mechanical connection between the head and the shank/body element.

2. A kit for assembly of a modular joint prosthesis for replacement of a head, neck and adjacent portions of a bone of the joint, the kit comprising:
   at least two stem-body elements, with each element sized for insertion into the shank of the bone; and
   at least two head members with each head member sized to replace one of the bearing surfaces of the joint, each stem-body element comprising an upper collar to lie adjacent the resected level of the bone, said collar providing a male taper at its outer diameter, each head member providing a corresponding female taper for receiving the male taper of each stem-body element, the engagement of the female taper on the male taper providing the sole mechanical connection between the head and the stem-body element;
   wherein each said collar terminates above said male taper and each said head member is formed with a concave inner surface providing, at its radially outer extent, said female taper to define above said collar a hollow space, said stem-body element providing a passageway for venting said hollow space.

3. A kit for assembly of a modular joint prosthesis for replacement of a head, neck and adjacent portions of a bone of the joint, the kit comprising:
   at least two stem-body elements, with each element sized for insertion into the shank of the bone; and
   at least two head members with each head member sized to replace one of the bearing surfaces of the joint, each stem-body element comprising an upper collar to lie adjacent the resected level of the bone, said collar providing a male taper at its outer diameter, each head member providing a corresponding female taper for receiving the male taper of each stem-body element, the engagement of the female taper on the male taper providing the sole mechanical connection between the head and the stem-body element;

wherein each said collar terminates above said male taper and each said head member is formed with a concave inner surface providing said female taper to define above said collar a hollow space, said stem-body element and said head member cooperating to define a passageway for venting said hollow space.

4. A joint prosthesis, comprising:

an integral stem and body, the body including a collar having a first taper; and a head having a second taper;

wherein engagement of the first taper with the second taper provides a mechanical connection between the head and the body; and wherein the first taper is discontinuous to vent a space defined between the collar and head when the first taper is engaged with the second taper.

5. A joint prosthesis, comprising:

an integral stem and body, the body including a collar having a first taper; and a head having a second taper;

wherein engagement of the first taper with the second taper provides a mechanical connection between the head and the body; and wherein the second taper is discontinuous to vent a space defined between the collar and head when the first taper is engaged with the second taper.

6. A joint prosthesis, consisting essentially of:

an integral stem and body, the body including a collar having a male taper toward a complementary bearing surface to the prosthesis;

and a head having a complementary female taper corresponding to the male taper of the collar to receive the collar in the assembled joint;

wherein a space is defined between the collar and head in the assembled configuration and the body and stem define a vent passageway extending between the space and a location on the stem remote from the head.

7. A joint prosthesis, comprising:

a first component and a second component, the second component consisting essentially of an integral stem and body, the body including a collar having a male taper toward the first component in the assembled joint; and a head having a complementary female taper corresponding to the male taper of the collar to receive the collar in the assembled joint;

wherein the male taper is discontinuous to vent a space defined between the collar and head in an assembled configuration.

8. A joint prosthesis, comprising:

a first component and a second component, the second component consisting essentially of an integral stem and body, the body including a collar having a male taper toward the first component in the assembled joint;

and a head having a complementary female taper corresponding to the male taper of the collar to receive the collar in the assembled joint;

wherein the female taper is discontinuous to vent a space defined between the collar and head in an assembled configuration.

9. A joint prosthesis, comprising:

a first component and a second component, the second component consisting essentially of an integral stem and body, the body including a collar having a male taper toward the first component in the assembled joint; and a head having a complementary female taper corresponding to the male taper of the collar to receive the collar in the assembled joint;

wherein a space is defined between the collar and head in the assembled configuration and the body and stem define a vent passageway extending between the space and a location on the stem remote from the head.

10. The joint prosthesis of claim 4, wherein:

said first taper is a male taper, and said second taper is a female taper.

11. The joint prosthesis of claim 5, wherein:

said first taper is a male taper, and said second taper is a female taper.

* * * * *